United States Patent
Romano et al.

(10) Patent No.: US 9,517,359 B2
(45) Date of Patent: Dec. 13, 2016

(54) HIGH INTENSITY FOCUSED ULTRASOUND DEVICE WITH A CONCAVE SEGMENT SHAPED TRANSDUCER FOR EYE TREATMENT

(75) Inventors: Fabrizio Romano, Rillieux-la-Pape (FR); Cyril Lafon, Lyons (FR); Jean-Yves Chapelon, Lyons (FR); Françoise Chavrier, Lyons (FR); Alain Birer, Lyons (FR); Laurent Farcy, Liergues (FR); Philippe Chapuis, Pommiers (FR)

(73) Assignees: EYE TECH CARE, Rillieux-la-Pape (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 122 days.

(21) Appl. No.: 13/202,079

(22) PCT Filed: Aug. 18, 2009

(86) PCT No.: PCT/EP2009/060678
§ 371 (c)(1),
(2), (4) Date: Aug. 17, 2011

(87) PCT Pub. No.: WO2010/094349
PCT Pub. Date: Aug. 26, 2010

(65) Prior Publication Data
US 2011/0301469 A1    Dec. 8, 2011

(30) Foreign Application Priority Data
Feb. 18, 2009    (EP) .................. PCT/EP2009/051892

(51) Int. Cl.
*A61B 8/14*    (2006.01)
*A61N 7/02*    (2006.01)
(Continued)

(52) U.S. Cl.
CPC ............. *A61N 7/02* (2013.01); *A61F 9/00745* (2013.01); *A61B 2018/00291* (2013.01);
(Continued)

(58) Field of Classification Search
CPC ...... G10K 11/30; G10K 11/32; A61F 9/00781
(Continued)

(56) References Cited

U.S. PATENT DOCUMENTS 4,163,394 A * 8/1979 Soldner .......................... 73/626
4,484,569 A    11/1984 Driller et al.
(Continued)

FOREIGN PATENT DOCUMENTS

DE    4430720 A1    6/1995
DE    20221042 U1    11/2004
(Continued)

OTHER PUBLICATIONS

Therapeutic ultrasound in the treatment of glaucoma I.-Experimental model—Coleman DJ & al., PMID:3991121 (PubMed), Mar. 1985, 92(3), 339-346 (Experimental model), and 347-353.
(Continued)

*Primary Examiner* — Serkan Akar
(74) *Attorney, Agent, or Firm* — McBee Moore Woodward Vanik IP LLC

(57) ABSTRACT

A device for treatment of an ocular pathology characterized in that it comprises at least one eye ring (1) wherein the proximal end of said eye ring (1) is suitable to be applied onto the globe and a generator (2,17) to generate ultrasound beam fixed on the distal end of the eye ring (1), the generator to generate ultrasound beam presenting a concave segment shape conformed along a single curvature corresponding to a single direction wherein the concavity is designed to be tuned towards the eyeglobe.

13 Claims, 9 Drawing Sheets

(51) Int. Cl.
*A61F 9/007* (2006.01)
*A61B 18/00* (2006.01)
*A61N 7/00* (2006.01)

(52) U.S. Cl.
CPC ... *A61F 9/00781* (2013.01); *A61N 2007/0065* (2013.01); *A61N 2007/0078* (2013.01); *A61N 2007/027* (2013.01)

(58) Field of Classification Search
USPC ........................................................ 600/459
See application file for complete search history.

(56) References Cited

U.S. PATENT DOCUMENTS

| | | | |
|---|---|---|---|
| 4,634,418 A | 1/1987 | Binder | |
| 4,787,885 A | 11/1988 | Binder | |
| 4,936,825 A | 6/1990 | Ungerleider | |
| 4,946,436 A | 8/1990 | Smith | |
| 5,127,901 A | 7/1992 | Odrich | |
| 5,180,362 A | 1/1993 | Worst | |
| 5,193,527 A * | 3/1993 | Schafer | 601/2 |
| 5,230,334 A | 7/1993 | Klopotek | |
| 5,360,399 A | 11/1994 | Stegmann | |
| 5,433,701 A | 7/1995 | Rubinstein | |
| 6,039,689 A | 3/2000 | Lizzi | |
| 6,267,752 B1 | 7/2001 | Svetliza | |
| 2002/0016557 A1 | 2/2002 | Duarte et al. | |
| 2004/0015140 A1 | 1/2004 | Shields | |
| 2006/0184072 A1* | 8/2006 | Manna | 601/2 |
| 2006/0241527 A1* | 10/2006 | Muratore et al. | 601/2 |
| 2007/0123814 A1* | 5/2007 | Roy | 604/20 |
| 2007/0203478 A1* | 8/2007 | Herekar | A61F 9/008 606/10 |
| 2007/0239011 A1 | 10/2007 | Lau et al. | |
| 2008/0189932 A1* | 8/2008 | Sliwa et al. | 29/594 |
| 2008/0262358 A1* | 10/2008 | Kaminski et al. | 600/459 |
| 2008/0275370 A1 | 11/2008 | McIntyre et al. | |
| 2009/0088623 A1* | 4/2009 | Vortman et al. | 600/411 |
| 2009/0227909 A1* | 9/2009 | Schafer et al. | 601/2 |

FOREIGN PATENT DOCUMENTS

| | | |
|---|---|---|
| EP | 0627207 A1 | 12/1994 |
| EP | 1243236 A1 | 9/2002 |
| EP | 1306068 A2 | 5/2003 |
| EP | 1325722 A2 | 7/2003 |
| EP | 1350492 A2 | 10/2003 |
| EP | 1738725 A1 | 1/2007 |
| RU | 2197926 C2 | 2/2003 |
| RU | 2200522 C1 | 3/2003 |
| SU | 591186 A1 | 2/1978 |
| WO | 96/14019 A1 | 5/1996 |
| WO | 96/28213 A1 | 9/1996 |
| WO | 01/80708 | 11/2001 |
| WO | 0238078 A2 | 5/2002 |
| WO | 2006/018686 | 2/2006 |
| WO | 2006/065671 | 6/2006 |
| WO | 2006/136912 | 12/2006 |
| WO | 2007/081750 A2 | 7/2007 |
| WO | 2008/024795 A2 | 2/2008 |

OTHER PUBLICATIONS

Muller, M. "Focusing water shock waves for lithotripsy by various ellipsoid reflectors", Biomed Tech (Berl), Apr. 1989, 34(4), 62-72.
Lizzi et al.,-"Ultrasonis therapy and imaging in ophtamology", vol. 14, Jan. 1985, pp. 1-17,XP00207983.
Etude opérationnelle réstrospective des coûts des deux premières années de traitement dans le glaucome primitif á angle ouvert et l'hypertension oculaire en France—Rouland et al, Fr. Ophtalmol., 2001, 24, 3, 233-243.
Bron et al."Prévalence de l'hypertonie oculaire et du glaucome dans une population française non sélectionnée", 2006, 29, 6, 635-641.
Chavrier et al."Modeling of high-intensity focused ultrasound-induced lesions in the presence of cavitations bubbles", J. Acoust. Soc. Am., vol. 108, n°1, Jul. 2000.
Lachkar et al.- Dépistage du glaucoma chronique â angle ouvert, Encycl. Med. Chir.-Editions scientifiques et médicales Elsevier SAS-21-275-A-20, 2001 14p.
Dépistage et diagnostic précoce du glaucome : problématique et perspectives en France, recommandation en santé publique-Haute Autorité de Santé—Nov. 2006.
Traitement des glaucomes réfractaires, Pascale Hamard—1997—Editions scientifiques et médicales Elsevier SAS.
International Search Report Based on International Application No. PCT/EP2009/060678 Mailed March 4, 2010.

\* cited by examiner

HIGH INTENSITY FOCUSED ULTRASOUND DEVICE WITH A CONCAVE SEGMENT SHAPED TRANSDUCER FOR EYE TREATMENT

CROSS REFERENCE TO RELATED APPLICATIONS

This application is a §371 National Stage Application of PCT/EP2009/060678 filed Aug. 18, 2009, which claims priority to PCT/EP2009/051892 filed Feb. 18, 2009.

BACKGROUND OF THE INVENTION

Field of the Invention

The present invention is generally directed to a non invasive treatment for ocular pathology, and relates more particularly to a device and method for generating high intensity focused ultrasound onto at least one annular segment of the ciliary body of an eye affected by glaucoma Description of Related Art In the field of ophthalmologic disease, it is well known that glaucoma is a significant public health problem, between 1 to 2% of population being suffering from this pathology, because glaucoma is a major cause of blindness.

The World health organisation considers glaucoma as the second cause of blindness in the world, responsible of 15% of declared blindness occurrences, with an incidence of 2.4 millions persons per year.

The evolution of glaucoma is slow. Glaucoma is an insidious health disease because at the first stage glaucoma is asymptomatic; the patient does not feel any pain or any visual problem. When the first visual troubles appear, lesions are commonly already large and despite irreversible.

The blindness that results from glaucoma involves both central and peripheral vision and has a major impact on an individual's ability to lead an independent life.

Glaucoma is an optic neuropathy, i.e. a disorder of the optic nerve, which usually occurs in the setting of an elevated intraocular pressure. The pressure within the eye increases and this is associated with changes in the appearance and function of the optic nerve. If the pressure remains high for a long period of time (many years), total vision loss occurs. High pressure develops in an eye because of an internal fluid imbalance.

The eye is a hollow structure composed of two segments: the anterior segment between the cornea and the crystalline lens, and the posterior segment between the crystalline lens and the retina. The anterior segment contains a clear fluid called "aqueous humor." Aqueous humor is formed in the posterior chamber of the anterior segment of the eye by the ciliary body. The fluid, which is made at a fairly constant rate, then passes around the lens, through the pupillary opening in the iris and into the anterior chamber of the eye. The fluid drains out of the eye mainly through the trabecular meshwork and Schlemm's canal.

With the increased pressure in the eye, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to abnormally elevated IOP than other eyes.

The only therapeutic approach currently available in glaucoma is to reduce the intraocular pressure. The objective is not to restore lost vision, because lesions are not reversible, but to preserve residual vision.

The clinical treatment of glaucoma is approached in a step-wise fashion. Medication often is the first treatment option except for congenital glaucoma wherein surgery is the primary therapy.

Administered either topically or orally, these medications work to either reduce aqueous production or they act to increase outflow. Currently available medications may have many serious side effects including: congestive heart failure, respiratory distress, hypertension, depression, renal stones, aplastic anemia, sexual dysfunction and death.

The commonly used medications are Prostaglandin or analogs like latanoprost (Xalatan), bimatoprost (Lumigan) and travoprost (Travatan) which increase uveoscleral outflow of aqueous humor; Topical beta-adrenergic receptor antagonists such as timolol, levobunolol (Betagan), and betaxolol which decrease aqueous humor production by the ciliary body; Alpha2-adrenergic agonists such as brimonidine (Alphagan) which work by a dual mechanism, decreasing aqueous production and increasing uveo-scleral outflow; Less-selective sympathomimetics like epinephrine and dipivefrin (Propine) which increase outflow of aqueous humor through trabecular meshwork and possibly through uveoscleral outflow pathway; Miotic agents (parasympathomimetics) like pilocarpine which work by contraction of the ciliary muscle, tightening the trabecular meshwork and allowing increased outflow of the aqueous humour; Carbonic anhydrase inhibitors like dorzolamide (Trusopt), brinzolamide (Azopt), acetazolamide (Diamox) which provide a reduction of aqueous humor production by inhibiting carbonic anhydrase in the ciliary body. The two most prescribed medications are currently topical Prostaglandin Analogs and Betablockers.

Compliance with medication is a major problem, with estimates that over half of glaucoma patients do not follow their correct dosing schedules. Fixed combinations are also prescribed extensively since they improve compliance by simplifying the medical treatment.

When medication fails to adequately reduce the pressure, often surgical treatment is performed as a next step in glaucoma treatment. Both laser and conventional surgeries are performed to treat glaucoma. In many cases, these operations are a temporary solution, as there is not yet a cure which is completely satisfactory for glaucoma.

There are two different approaches to treat glaucoma: either the surgeon tries to improve aqueous humor drainage, or he tries to reduce its production.

The most practiced surgeries intended to improve the aqueous humor drainage are: canaloplasty, laser trabeculoplasty, laser peripheral iridotomy (in case of angle closure glaucoma), trabeculectomy, deep non perforating sclerectomy and glaucoma drainage implants.

The most practiced surgery intended to reduce aqueous humor production is the cyclodestruction technique. When cyclodestruction is performed with a laser, it is called cyclophotocoagulation. High Intensity focused Ultrasound can be used to obtain a cyclodestruction.

Canaloplasty is an advanced, non penetrating procedure designed to enhance and restore the eye's natural drainage system to provide sustained reduction of IOP. Canaloplasty utilizes breakthrough micro catheter technology in a simple and minimally invasive procedure. To perform a canaloplasty, a doctor will create a tiny incision to gain access to a canal in the eye. A micro catheter will circumnavigate the canal around the iris, enlarging the main drainage channel and its smaller collector channels through the injection of a sterile, gel-like material. The catheter is then removed and a suture is placed within the canal and tightened. By opening the canal, the pressure inside the eye will be relieved.

Laser trabeculoplasty may be used to treat open angle glaucoma. A laser spot is aimed at the trabecular meshwork to stimulate opening of the mesh to allow more outflow of aqueous fluid. Usually, half of the angle is treated at a time.

There are two types of laser trabeculoplasty:

Argon laser trabeculoplasty (ALT) uses a laser to open up the drainage angle of the eye.

Selective laser trabeculoplasty (SLT) uses a lower-level laser to obtain the same result.

Laser peripheral iridotomy may be used in patients susceptible to or affected by angle closure glaucoma. During laser iridotomy, laser energy is used to make a small full-thickness opening in the iris. This opening equalizes the pressure between the front and back of the iris, causing the iris to move backward.

The most common conventional surgery performed for glaucoma is the trabeculectomy. Here, a partial thickness flap is made in the scleral wall of the eye, and a window opening made under the flap to remove a portion of the trabecular meshwork. The scleral flap is then sutured loosely back in place. This allows fluid to flow out of the eye through this opening, resulting in lowered intraocular pressure and the formation of a bleb or fluid bubble on the surface of the eye.

Trabeculectomy is associated with many problems. Fibroblasts that are present in the episclera proliferate and migrate and can scar down the scleral flap. Failure from scarring may occur, particularly in children and young adults. Of eyes that have an initially successful trabeculectomy, eighty percent will fail from scarring within three to five years after surgery. To minimize fibrosis, surgeons now are applying antifibrotic agents such as mitomycin C (MMC) and 5-fluorouracil (5-FU) to the scleral flap at the time of surgery. The use of these agents has increased the success rate of trabeculectomy but also has increased the prevalence of hypotony. Hypotony is a problem that develops when aqueous flows out of the eye too fast. The eye pressure drops too low (usually less than 6.0 mmHg); the structure of the eye collapses and vision decreases. Antimetabolites directly applied on the surgical site can be used in order to improve the surgical prognosis, especially in high risk of failure (black patients, juvenile glaucoma . . . ).

Trabeculectomy creates a pathway for aqueous fluid to escape to the surface of the eye. At the same time, it creates a pathway for bacteria that normally live on the surface of the eye and eyelids to get into the eye. If this happens, an internal eye infection can occur called endophthalmitis. Endophthalmitis often leads to permanent and profound visual loss. Endophthalmitis can occur anytime after trabeculectomy. Another factor that contributes to infection is the placement of a bleb. Eyes that have trabeculectomy performed inferiorly have about five times the risk of eye infection than eyes that have a superior bleb. Therefore, initial trabeculectomy is performed superiorly under the eyelid, in either the nasal or temporal quadrant.

In addition to scarring, hypotony and infection, there are other complications of trabeculectomy. The bleb can tear and lead to profound hypotony. The bleb can be irritating and can disrupt the normal tear film, leading to blurred vision. Patients with blebs generally cannot wear contact lenses. All of the complications from trabeculectomy stem from the fact that fluid is being diverted from inside the eye to the external surface of the eye.

More recently a new surgical technique has been described, called Non-perforating deep sclerectomy ab externo. This technique allows avoiding to open the anterior chamber of the eye and consequently reduces the risk of postoperative complications. The major limitation of this technique is that it is a very difficult surgical technique and only a few surgeons are able to perform it successfully.

When trabeculectomy or sclerectomy doesn't successfully lower the eye pressure, the next surgical step often is an aqueous shunt device. There are several different glaucoma drainage implants. These include the original Molteno implant, the Baerveldt tube shunt, or the valved implants, such as the Ahmed glaucoma valve implant or the ExPress Mini Shunt and the later generation pressure ridge Molteno implants. These are indicated for glaucoma patients not responding to maximal medical therapy, with previous failed guarded filtering surgery (trabeculectomy). The flow tube is inserted into the anterior chamber of the eye and the plate is implanted underneath the conjunctiva to allow flow of aqueous fluid out of the eye into a chamber called a bleb.

The prior art includes a number of such aqueous shunt devices, such as U.S. Pat. No. 4,936,825, U.S. Pat. No. 5,127,901, U.S. Pat. No. 5,180,362, U.S. Pat. No. 5,433,701, U.S. Pat. No. 4,634,418, U.S. Pat. No. 4,787,885, U.S. Pat. No. 4,946,436, U.S. 20040015140A1 and U.S. Pat. No. 5,360,399.

Many complications are associated with aqueous shunt devices. A thickened wall of scar tissue that develops around the plastic plate offers some resistance to outflow and in many eyes limits the reduction in eye pressure. In some eyes, hypotony develops because the flow through the tube is not restricted. The surgery involves operating in the posterior orbit and many patients develop an eye muscle imbalance and double vision post-operatively. Moreover, because they are open to the surface of the eye, a pathway is created for bacteria to get into the eye and endophthalmitis can potentially occur.

All the strategies mentioned above are intended to improve aqueous humor drainage. Another strategy consists in destroying a significant proportion of a circular intraocular organ, placed behind the iris: the ciliary body. This organ and particularly the double layer epithelium cells are responsible for aqueous humor production. The destruction of a significant proportion of the ciliary body, technique called cyclodestruction, reduces the production of aqueous humor and consequently reduces the Intra Ocular Pressure.

The most common technique currently used is the cyclophotocoagulation obtained with a laser diode (810 nm). During cyclophotocoagulation surgery, the surgeons point a laser at the white part of the eye (sclera). The laser passes through the sclera to the ciliary body. The laser damages parts of the ciliary body so that it will produce less aqueous humor, which lowers eye pressure. The procedure is performed with local anaesthesia. The problem with cyclophotocoagulation is that one shot destroys only a small region of ciliary body and many shots are necessary all around the eye globe, so that a sufficient part of the ciliary body is destroyed. At each point the surgeon places manually the laser applicator in contact with the sclera approximately at 2 mm from the limbus and with an incidence ideally perpendicular to the surface of the eye. Then he performs a laser shot. Then he moves the applicator to the next site for a new laser shot. This manual technique is quite empiric, non reproducible, long and not easy. Moreover, the surgeon starts the laser shot without any control on the precise position and direction of the laser beam and without any feedback on the result of the shot on the ciliary body.

DE 44 30 720 describes an apparatus for diode laser cyclophotocoagulation to improve the technique and reduce the risk of empiric manipulation. As shown on FIGS. 2a and 3 of DE 44 30 720, the apparatus comprises laser means (3, 33) for applying laser radiation for cyclophotocoagulation, an ultrasonic head (4, 40) of an ultrasonic bio microscope for monitoring said laser cyclophotocoagulation, and fixing means for holding the laser means and the ultrasonic head.

The ultrasonic head generates low intensity ultrasounds to obtain high resolution echographic images of the region to be treated.

The fixing means serves both to stabilize the patient's eye in the course of the treatment and also to keep the liquid in place on the patient's eye. The fixing means comprise two cylinders: an outer cylinder 20a, and an inner cylinder 20b. The outer cylinder is adapted to be disposed on the eye of the patient. The inner cylinder is destined to support the laser means and the ultrasonic means. The inner cylinder is adjoined to the outer cylinder and is adapted to rotate relative to the outer cylinder.

As described in DE 44 30 720, during the treatment, the laser means generate laser radiations punctually for cyclophotocoagulation of a punctual zone of the region to be treated. Then, the ultrasonic head and the laser means are displaced by rotating the inner cylinder in order to treat another punctual zone of the region of interest. These steps are repeated until all the circumference of the eye has been treated.

This method presents the inconvenient that it is necessary to repeat the operation (i.e. rotate the inner cylinder, acquire an image, verify that the apparatus is still in place, produce a laser shot) many times to treat the whole region to be treated. In other words, the operation have to be repeated many times so that the all the circumference of the eye can be treated.

Furthermore, this method may induce damages to the visual functions (due to spot size errors, misalignment between the ultrasonic head, the laser means and the fixing means, etc.).

Moreover, considering the region which is treated (i.e. the eye) and the size of such apparatus, it is easy to imagine the difficulties of manipulating such apparatus, and in particular to rotate the inner cylinder comprising the laser means and the ultrasonic means without inducing displacements of the outer cylinder.

Finally, the need of repeating an operation many times increases the operative time and thus the error risk factor.

To overcome these drawbacks, it has been already imagined using controlled ultrasonic energy in the treatment of glaucoma. "Therapeutic ultrasound in the treatment of glaucoma. I. Experimental model—Coleman D J, Lizzi F L, Driller J, Rosado A L, Chang S, Iwamoto T, Rosenthal D—PMID: 3991121 (PubMed) 1985 March; 92(3): 339-46" discloses a treatment of glaucoma applying High Intensity Focused Ultrasound (HIFU) onto the ciliary body to provide filtration and focal disruption of ciliary epithelium treating elevated intraocular pressure in a non invasive manner. An apparatus associated to this treatment using controlled ultrasonic energy in the treatment of glaucoma is also described in U.S. Pat. No. 4,484,569. However, such apparatus which was manufactured and distributed under the commercial name of SONOCARE was very difficult to manipulate. Moreover such apparatus allows to treat only one punctual zone at a time. Thus—as disclosed above with regard to laser techniques—each shot needs to be repeated many time to treat all the circumference of the eye and all the apparatus needs to be handled, placed and calibrated many times, thus taking a very long time (i.e. displacement of the ultrasonic means, verification of the position of the ultrasonic means with regard to the punctual region to be treated with optical and echographic sighting means, filling of the device with coupling liquid and production of a ultrasonic shot).

In the same manner, the prior art includes the international patent application WO 02/38078 teaching a method of treating an eye, including glaucoma, that comprises the steps of identifying an area of an eye, such as Schlemm's canal for example, focusing a device capable of directing HIFU energy on the area, such as transducer of 4 to 33 mm range, generating HIFU energy from the device onto the area wherein the energy transfer from the device to the area results in an increase in temperature of the area.

Even if this method provides a treatment to glaucoma in a non invasive manner, it presents the inconvenient that it is necessary to repeat the operation many times to treat the eye circumferentially.

Moreover, tissues at the neighbourhood of the treatment area can be destroyed leading to blurred vision, eye muscle imbalance or double vision. It is therefore necessary to use an imaging system like a scan ultrasonography or a Magnetic Resonance Imaging system said MRI to identify the area to be treated with the greatest precision and to measure changes in the subject eye after each operation.

It is consequently hard and expensive to apply this method in the treatment of glaucoma.

SUMMARY OF THE INVENTION

There is a need for an accurate, safe, effective and inexpensive method of treating an ocular pathology by applying easily and safely high intensity focused ultrasound onto the eye to be treated and for a device thereof.

The above-mentioned need is addressed by the embodiments described herein in the following description of the invention which allows unlike other laser or HIFU treatments to treat the whole circumference of the eye in only one step, without the necessity to manipulate the device during the procedure.

In one embodiment, a device for treatment of an ocular pathology is disclosed.

Said device comprises at least one eye ring wherein the proximal end of said eye ring is suitable to be applied onto the globe and means to generate ultrasound beam fixed on the distal end of the eye ring.

Said means fixed on the distal end of the eye ring are suitable to generate high intensity focused ultrasound beam.

DETAILED DESCRIPTION OF A PREFERRED EMBODIMENT

Figure 1:
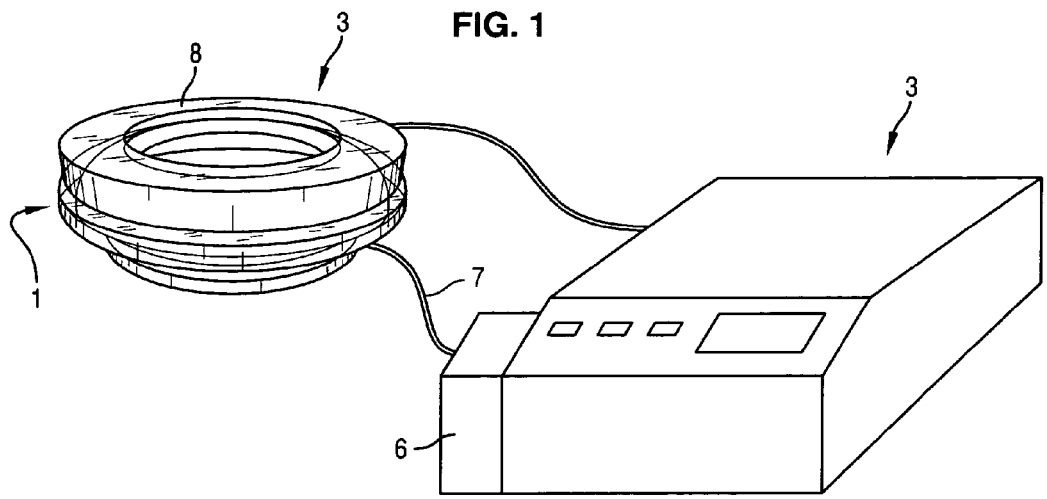
FIGS. 1-17 represent embodiments as described herein.

According to another embodiment of the invention, said means fixed on the distal end of the eye ring are suitable to generate scattered ultrasound beam.

The eye ring consists in a sawn-off cone element open at both ends wherein the small base is the proximal end and the large base is the distal end.

The proximal end of the sawn-off cone element comprises an external annular flange suitable to be applied onto the eye globe.

The proximal edge of the sawn-off cone element comprises an annular groove communicating with at least one hose formed in the sawn-off cone element and connected to a suction device.

The internal diameter of the proximal end of the sawn-off cone element is sensibly equal to the corneal diameter plus 2 to 6 mm, and more preferably equal to the sum of the corneal diameter with a value of 4 millimeters.

The internal diameter of the proximal end of the sawn-off cone element, depending on the patient corneal diameter, can be comprised between 12 and 18 mm and the internal diameter of the distal end of the sawn-off cone element can be comprised between 26 and 34 mm.

Moreover, the height of the sawn-off cone element is comprised between 8 and 12 mm.

The sawn-off cone element is in medical grade polymer.

Said means to generate high intensity focused ultrasound energy consists in at least two transducers and more preferably 6 transducers, fixed on the distal end of the sawn-off cone element in such a way that said transducers extend toward the revolution axis of said sawn-off cone element.

Said transducers can be made either in piezocomposite material or in piezoceramic material or in other materials which complies with the production of High Intensity Ultrasound. Said transducers can be focused by themselves and have a toric geometry, or a cylindrical geometry or a spherical geometry, or an elliptical geometry or they can be flat and be used in combination with a focusing system like acoustic lens or acoustic reflectors, with a variety of shapes and materials, extending under or in front of said flat transducers. Acoustic reflectors are well known in therapeutic ultrasound and are currently routinely used in external shockwave lithotripsy (Focusing water shock waves for lithotripsy by various ellipsoid reflectors—Müller M.—Biomed Tech (Berl). 1989 April; 34(4):62-72).

According to another embodiment of the invention, said means to generate high intensity dynamically focused ultrasound energy consists in at least two flat transducers having a cylindrical segment shape, fixed on the distal end of the sawn-off cone element in such a way that said transducers extend toward the revolution axis of said sawn-off cone element.

Alternatively, said means to generate scattered ultrasound beam are means to generate high intensity non focused ultrasound energy consisting in at least two transducers having an annular flat segment shape, fixed on the distal end of the sawn-off cone element in such a way that said transducers extend toward the revolution axis of said sawn-off cone element.

Moreover, said transducers are connected to a control unit.

Said device comprises two pairs of three transducers separated by two inactive sectors.

Transducers are successively activated by the control unit or simultaneously activated by said control unit.

One advantage of the device according to the present invention is that the means to generate ultrasound beam fixed on the distal end of the eye ring comprise a plurality of transducers arranged according to a treatment pattern.

This allows treating the eye circumferentially in one time. Indeed, unlike the methods and apparatuses described for instance in U.S. Pat. No. 4,484,569 and in DE 44 30 720, the apparatus according to the invention allows treating the eye without the need to repeat an operation many times.

With regard to U.S. Pat. No. 4,484,569 and DE 44 30 720, the invention allows in particular:

simplifying the operation procedure by providing a device which allows a treatment of the eye in one time; indeed, once the apparatus is placed and fixed onto the eye, the apparatus stay in position and the treatment of the whole circumference of the eye can be realized without the need for the operator to displace or maintain the apparatus, providing a reproducible procedure; indeed unlike the apparatus of the prior art, the device of the present invention do not need to be displaced many times to treat different punctual zones of the region to be treated, generating extended lesions covering large regions of the ciliary body unlike the apparatus of the prior art which generates only punctual lesions and needs many elementary lesions to be effective, reducing the operative time which reduces the risk factor for the patient and thus improve the quality of the treatment, providing a treatment which is less dependent from the operator, because very easy to be performed, very easy to be learned with an extremely short learning curve, and relatively automatic during the treatment time.

In a preferred embodiment, the invention relates to a device for treatment of an ocular pathology, the device comprising at least one eye ring wherein the proximal end of said eye ring is suitable to be applied onto the globe and means to generate ultrasound beam fixed on the distal end of the eye ring, said means to generate ultrasound beam presenting a concave segment shape conformed along a single curvature corresponding to a single direction wherein the concavity is designed to be tuned towards the eyeglobe.

Preferably, the single direction is perpendicular to the revolution axis of the eye ring.

The use of means to generate ultrasound beam presenting a concave segment shape conformed along a single curvature corresponding to a single direction instead of means to generate ultrasound beam having a toric geometry allows eliminating the risk of having a plurality (at least two) focalisation regions, simplifying the manufacturing process making it possible to manufacture various diameters of the means to generate ultrasound beam without changing tools, obtaining a lesion shape which is almost identical to that obtained with toric elements.

In one embodiment of the present invention, the means to generate high intensity focused ultrasound energy comprise a standing crown holding at least two transducers having a concave segment shape conformed along the single curvature corresponding to the single direction, said standing crown being fixed on the distal end of the eye ring in such a way that the transducers extend toward the revolution axis of said eye ring.

In another embodiment, the means to generate high intensity focused ultrasound energy comprise a standing crown holding at least two transducers and a at least two focusing acoustic elements extending under a respective transducer, each focusing acoustic element having a concave segment shape conformed along the single curvature corresponding to the single direction, said standing crown being fixed on the distal end of the eye ring in such a way that the focusing acoustic element extend toward the revolution axis of said eye ring. Each transducer can be a flat segment having a globally rectangular profile that extends sensibly parallel to the proximal and distal edge of the eye ring.

Advantageously, the concave segment shape can be a cylindrical segment shape or an elliptical segment shape.

Preferably, the transducers are arranged according to a treatment pattern.

It will be understood in the case of the present invention that the treatment pattern corresponds to the form defined by the regions to be treated. In the case of the treatment of the ciliary bodies, the treatment pattern may be annular or semi-annular.

For instance, in one embodiment, the transducers can be placed peripherally over the standing crown according to the treatment pattern. More preferably, the transducers are placed peripherally over the whole or a part of the standing crown. In particular, the transducers can be placed circumferentially over the whole or a part of the circumference of the standing crown.

Embodiments of varying scope are described herein. In addition to the aspects described in this summary, further aspects will become apparent by reference to the drawings and with reference to the detailed description that follows.

Figure 2:
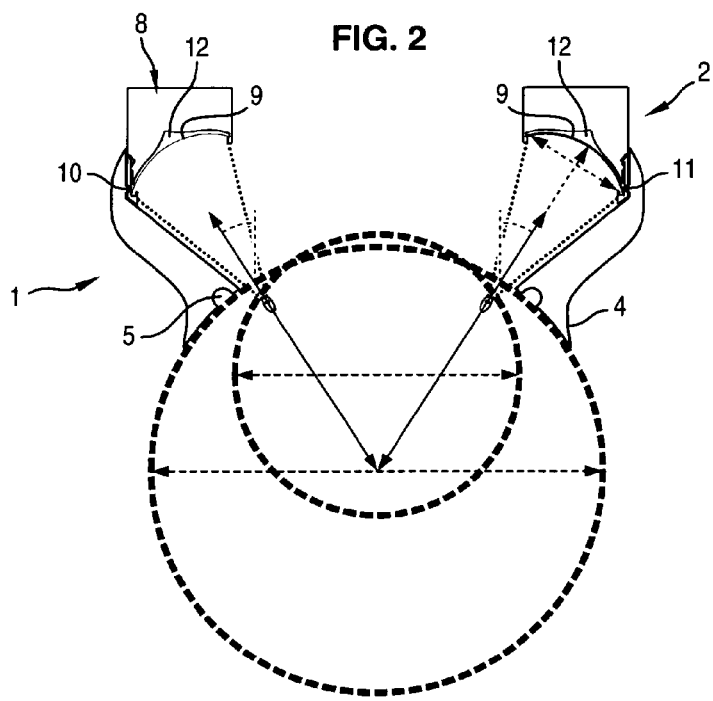
Figure 3:
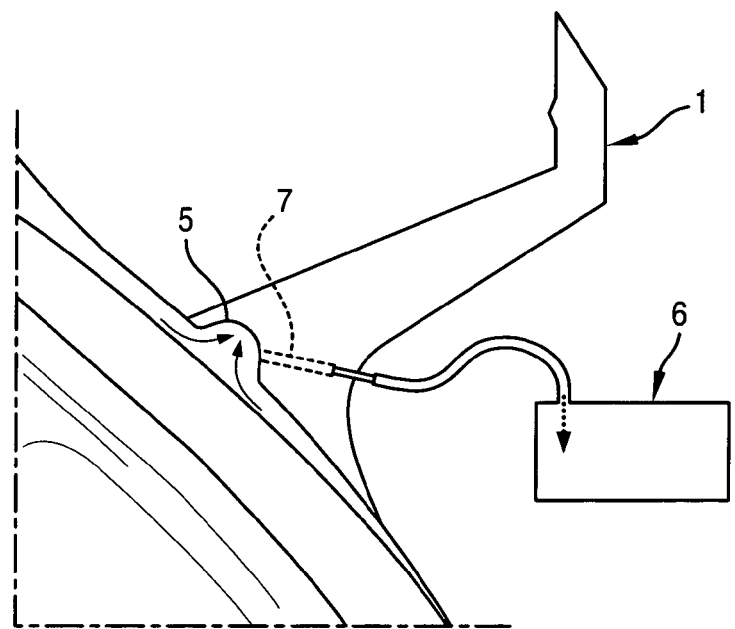
Figure 4:
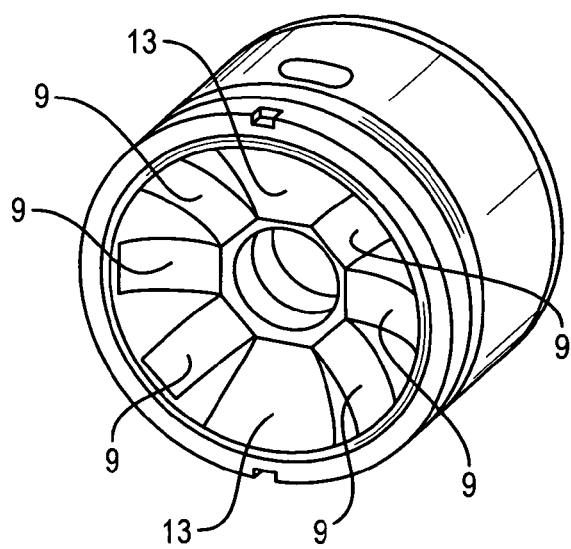
Figure 5:
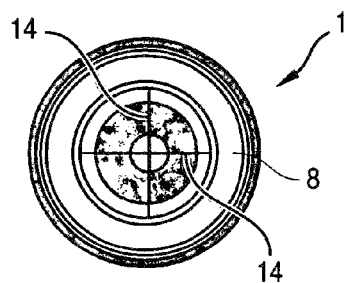
Figure 6:
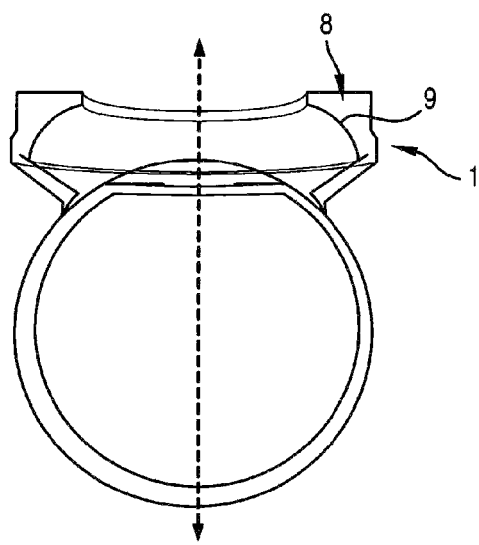
Figure 7:
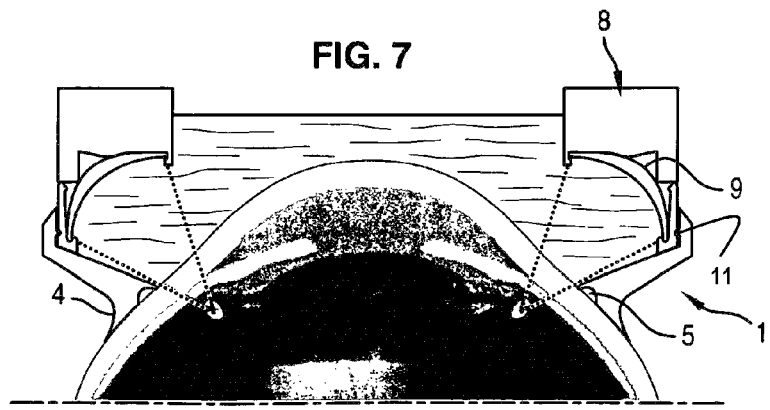
Figure 8:
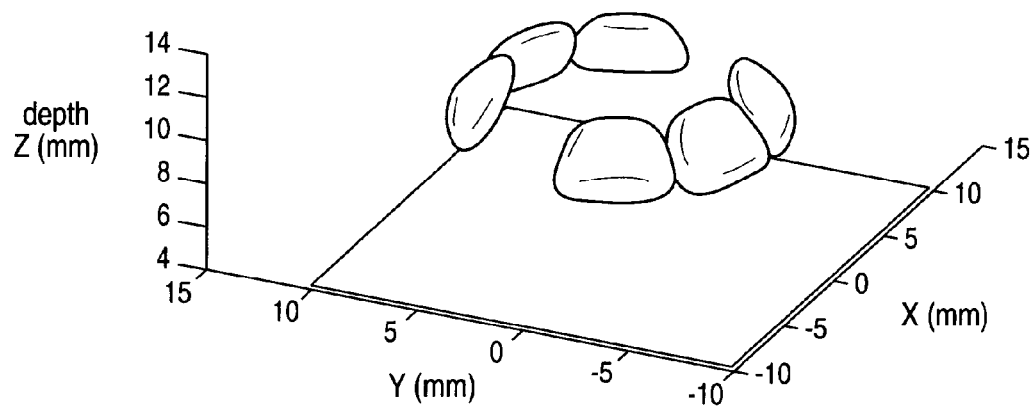
Figure 9:
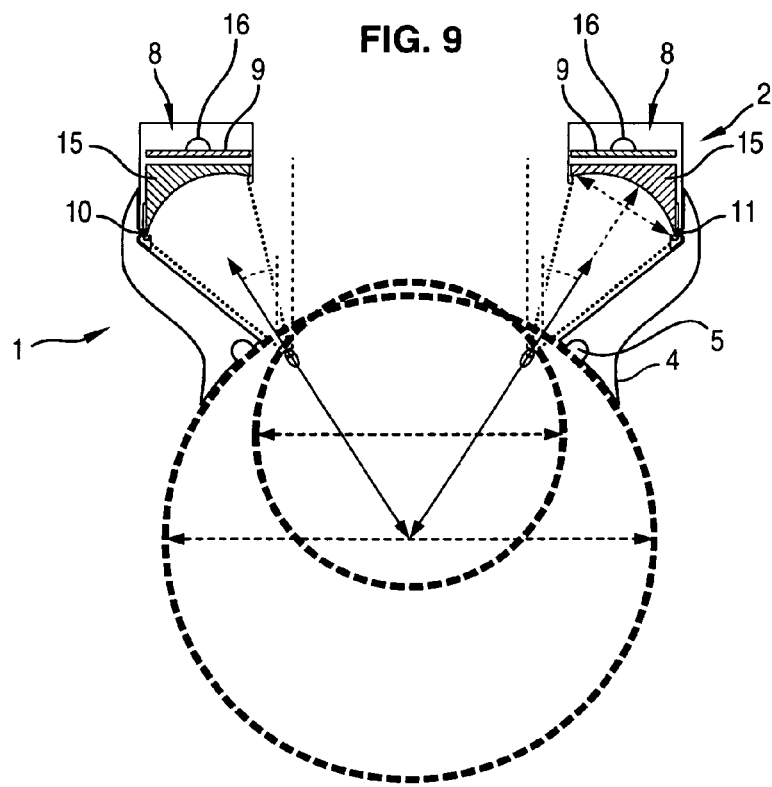
Figure 10:
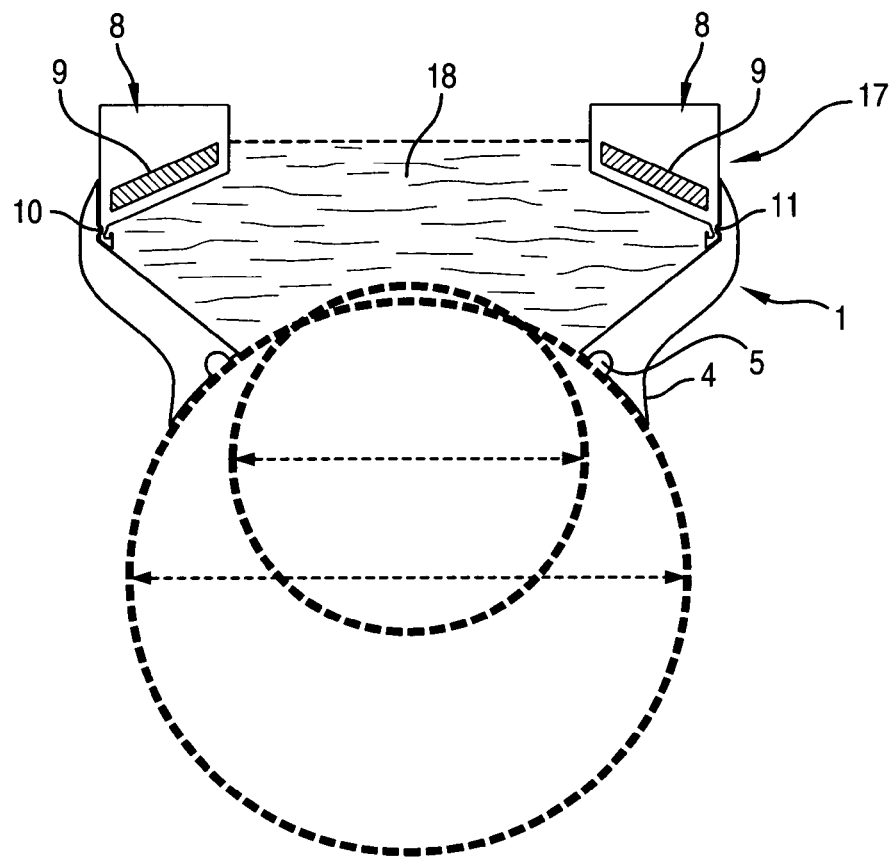

FIG. 1 is a schematic perspective view of the device for treatment of an ocular pathology by applying high intensity focused ultrasound according to the invention, FIG. 2 is an elevation view of the device according to the invention positioned to an eye to be treated, FIG. 3 is a partial view in elevation of the eye ring of the device according to the invention, FIG. 4 is a top view of the transducers held by the eye ring of the device according to the invention, FIG. 5 is a top view of the device correctly positioned to the eye to be treated, FIG. 6 is an elevation view of the device correctly positioned to the eye to be treated shown in FIG. 5, FIG. 7 is an elevation view of the device during the generation of HIFU energy, FIG. 8 is a 3D representation of the injured areas by HIFU energy according to the invention, FIG. 9 is an elevation view of another embodiment of the device according to the invention positioned to an eye to be treated, FIG. 10 is an elevation view of a last embodiment of device according to the invention particularly adapted for increasing the rate of transport of drug through eye tissue, FIGS. 11 to 17 illustrate different embodiments of means to generate ultrasound beam of the present invention.

We will disclose hereinafter a method and a device suitable for the treatment of glaucoma; nevertheless, it is obvious that the skilled person could adapt the method and the device for the treatment of any ophthalmologic pathology that necessitate surgery without departing of the scope of the invention.

Referring to FIG. 1, the device according to the invention comprises an eye ring 1 wherein the proximal end of said eye ring is suitable to be applied onto the globe of the eye to be treated and (see FIG. 2) means 2 to generate high intensity focused ultrasound energy, said means being fixed on the distal end of the eye ring. Said means are connected to a control unit 3 including a burst generator and means specifying the parameters of the burst such as the frequency, the power and the duration of each burst, the number of bursts (i.e. the number of transducers to be activated), etc. . . . . The burst generator comprises at least a sine-wave signal generator at a determined frequency comprised between 5 and 15 MHz, and preferably between 7 and 10 MHz, an amplifier and a Power meter.

Referring to FIGS. 1 and 2, the eye ring 1 consists in a sawn-off cone element opened at both ends wherein the small base is the proximal end and the large base is the distal end.

Referring to FIG. 2, the proximal end of the sawn-off cone element 1 comprises an external annular flange 4 suitable to be applied onto the external surface of the eyeglobe, at approximately 2 mm of the limbus, the limbus being the junction between the cornea and sclera of the eyeglobe. The proximal face of the annular flange 4 presents a concave profile, the radius of curvature of the concave profile being substantially equal to the radius of curvature of the eyeglobe.

Moreover, the proximal edge of the sawn-off cone element 1 comprises an annular groove 5 connected to a suction device 6 (FIG. 1) by at least one hose 7 passing through the sawn-off cone element 1 and emerging into the annular groove, said suction device 6 being advantageously controlled by the control unit 3.

It is obvious that the suction device 6 can be independent without departing from the scope of the invention.

When the sawn-off cone element 1 is applied onto the eye and the suction device 6 is operated, the depression into the annular groove 5 provide a deformation of the conjunctiva of the eye, said deformation forming an o-ring in the annular groove 5. The sawn-off cone element 1 is then closely interlinked in such a manner that said sawn-off cone element 1 will follow the micro movements of the eye during the whole treatment time taking less than 2 minutes, and maintaining the quality of the centred position of the device on the visual axis.

The sawn-off cone element 1 is advantageously obtained in medical grade silicon which is a soft material compatible with the conjunctiva contact.

It is obvious that the sawn-off cone element 1 can be obtained in any suitable material for medical purposes well known by the skilled person, and which has been verified as biocompatible, such as biocompatible PVC, without departing with the scope of the invention.

Referring to FIGS. 1 and 2, means 2 to generate high intensity focused ultrasound beam consist in a standing crown 8 holding a plurality of transducers 9 wherein the external radius of said standing crown 8 is sensibly equal to the internal diameter of the distal end of the sawn-off cone element 1. The external edge of the standing crown 8 of transducers 9 comprises an annular groove 10 cooperating with an annular lug 11 extending in the sawn-off cone element 1 at the vicinity of it's distal end in such a way that the standing crown 8 is retained at the distal end of the sawn-off cone element 1. In this way, the standing crown 8 extends toward the revolution axis of said sawn-off cone element 1. Said transducers 9 are held in the proximal edge of the standing crown 8. Moreover, each transducer 9 is a segment having a concave profile, wherein the concavity is tuned towards the eyeglobe, and more particularly towards the ciliary body as shown in FIG. 2. The proximal edge of the standing crown 8 comprises an annular groove 12 in which extends the connecting cables of the transducers 9, not shown in FIG. 2.

The transducers can be made either in piezocomposite material or in piezoceramic material or in other materials which complies with the production of High Intensity Ultrasound. Said transducers can be focused by themselves and have a toric geometry, or a cylindrical geometry or a spherical geometry, or an elliptical geometry.

Figure 11:
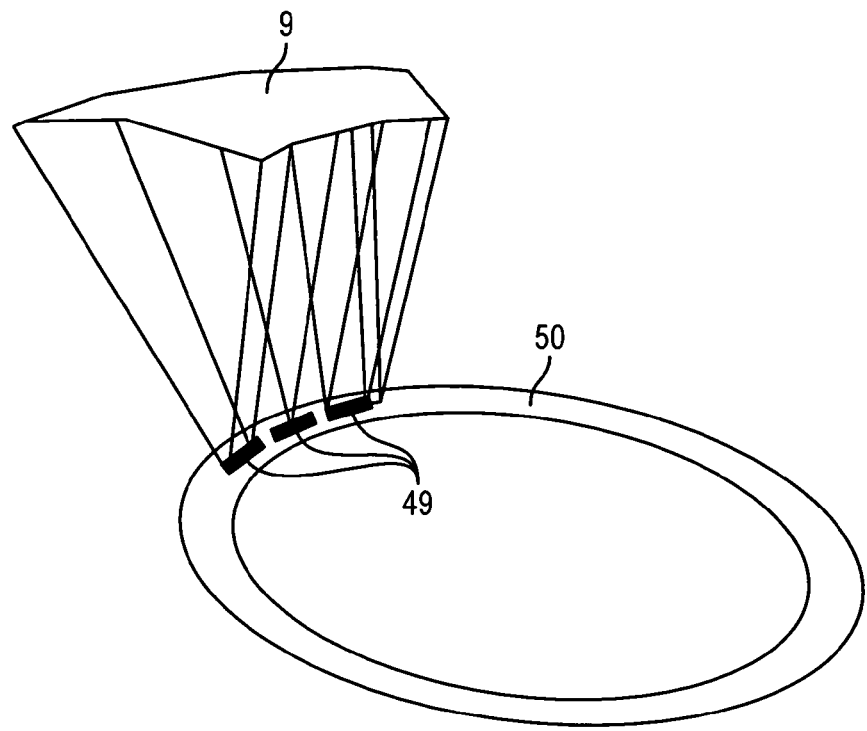

As shown on FIG. 11, the use of transducers 9 having a toric shape allows obtaining a lesion volume 49 having a shape of an arc of circle which corresponds to the annular shape of the ciliary body 50.

Figure 12A:
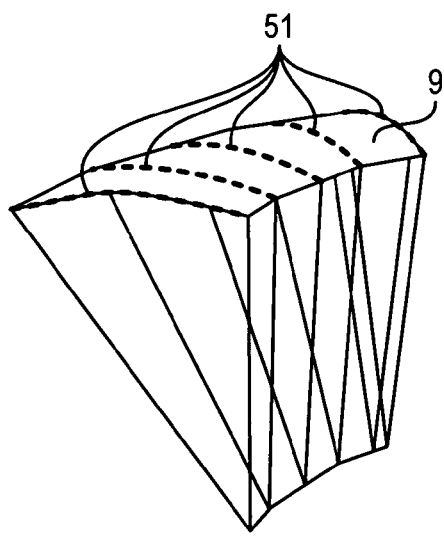

As shown on FIG. 12a, the radial radiuses 51 of curvature of transducers 9 having a toric geometry are all identical.

Figure 12B:
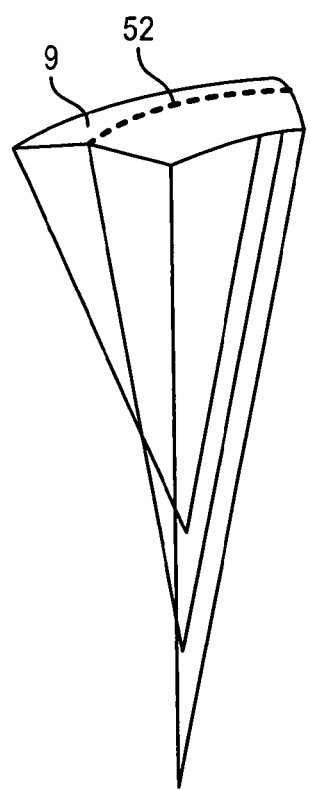

However, as shown on FIG. 12b, the concentric radiuses 52 of curvature of transducers 9 having a toric geometry are all different.

Figure 13A:
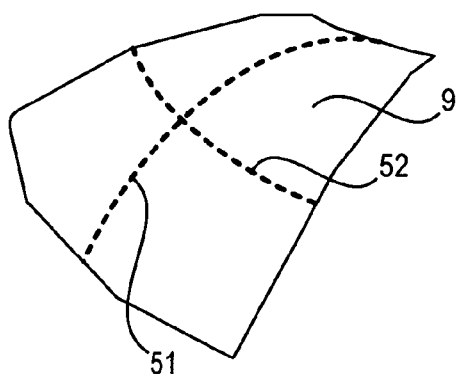
Figure 13B:
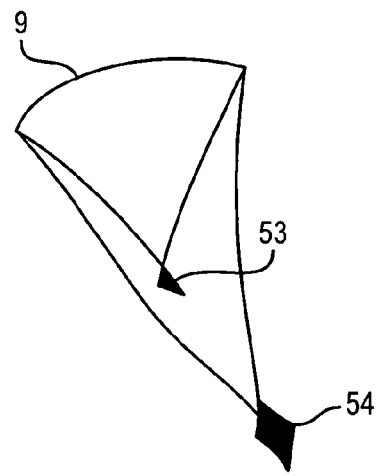

This implies that the ultrasound beams generated by the transducers 9 may focus on two different regions 53, 54 due to the two radiuses of curvature 51, 52 of the toric shape (see FIG. 13a, 13b).

Figure 14:
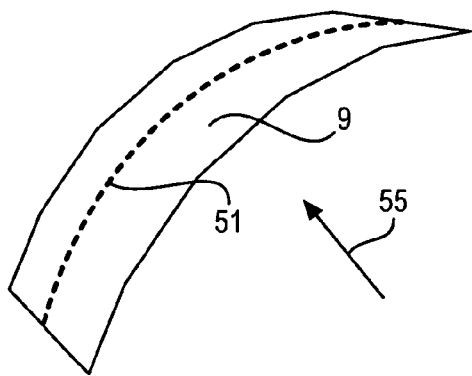

To overcome this drawback, transducers 9 having a geometry presenting a single radius of curvature 51 are preferred (see FIG. 14).

More precisely, the transducers 9 preferably present a concave segment shape conformed along a single curvature corresponding to a single direction 55 wherein the concavity is designed to be tuned towards the eyeglobe.

Figure 15:
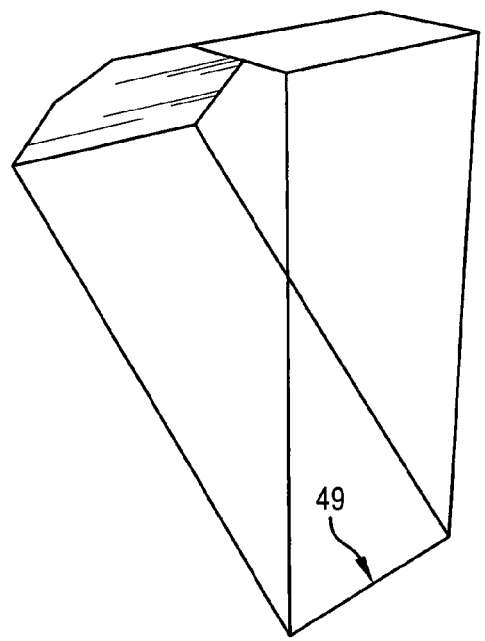
Figure 16:
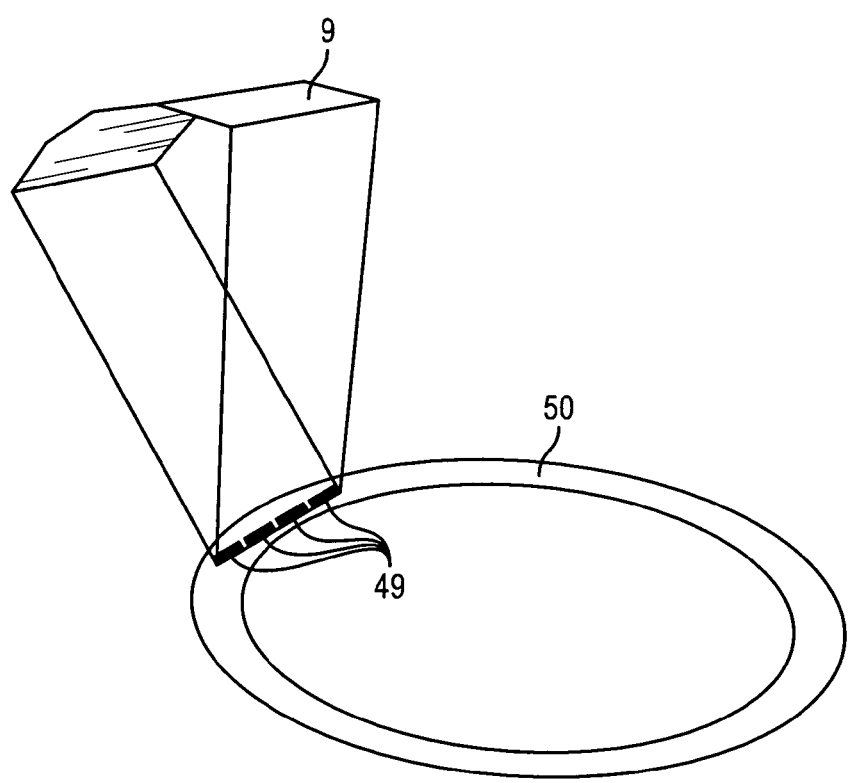

As shown on FIG. 15, the lesion 49 obtained using transducers 9 having a single radius of curvature 51 is not an arc de circle anymore, but a line segment. This line segment is inscribed in the annular shape of the ciliary body 50.

Preferably, the single direction is perpendicular to the revolution axis of the eye ring. This allows obtaining a lesion volume conformed along a line segment parallel to the ciliary body.

It has to be noticed that a transducer having a toric trapezoidal segment shape, due to a greater active surface, presents better conversion efficiency than a transducer having a rectangular geometry presenting a single radius of curvature. For a given electrical power, the acoustic power concentrated on a focal line is greater with a transducer having a toric segment shape than with a transducer having a geometry presenting a single radius of curvature. To overcome this drawback, the length of transducers having a geometry presenting a single radius of curvature is chosen greater than the length of corresponding transducers having a toric segment shape.

Each transducer can be made of a single segment curved along a single curvature corresponding to a single direction a single radius of curvature so as to define the concave segment shape of the transducer.

The transducers 9 can be flat and be used in combination with a focusing system like acoustic lens or acoustic reflectors, with a variety of shapes and materials, extending under or in front of said flat annular transducers. Acoustic reflectors are well known in therapeutic ultrasound and are currently routinely used in external shockwave lithotripsy (Focusing water shock waves for lithotripsy by various ellipsoid reflectors—Müller M.—Biomed Tech (Berl). 1989 April; 34(4):62-72).

In this case, the acoustic reflectors preferably have a geometry presenting a single radius of curvature for the reason explained above.

Figure 17:
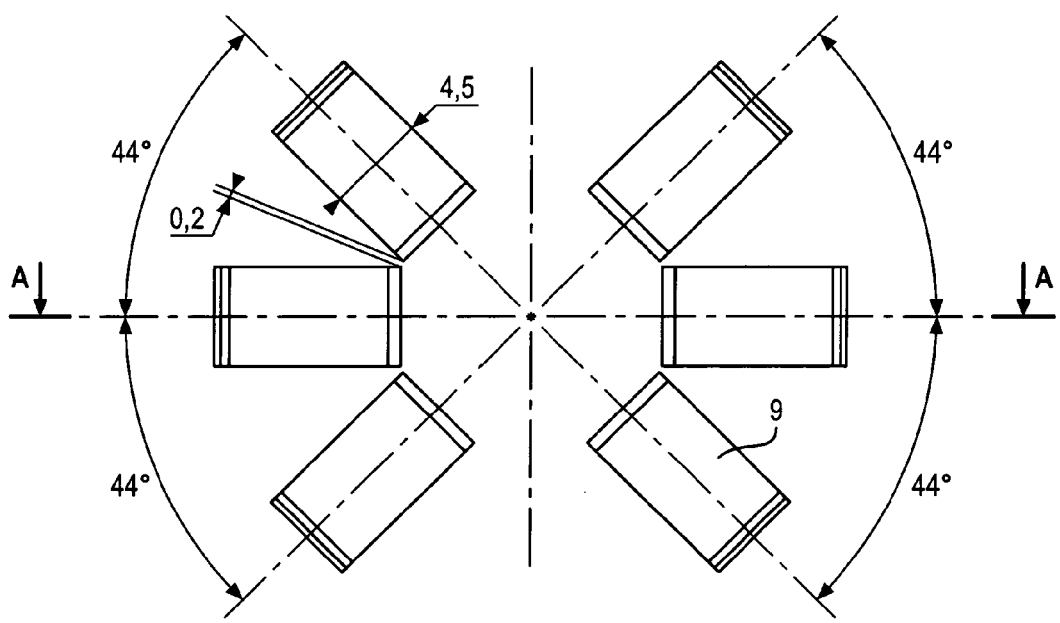
Figure 17:
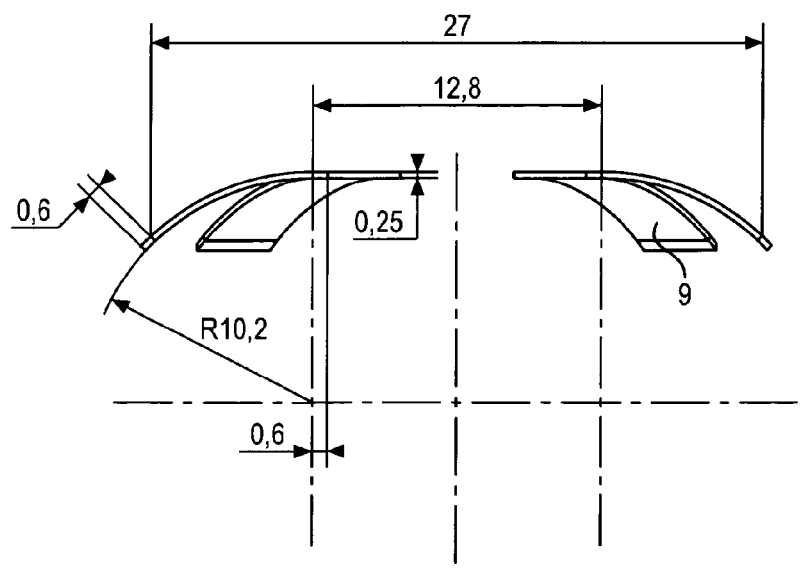

Referring to FIGS. 4 and 17, the standing crown 8 of transducers 9 comprises two pairs of three transducers 9 separated by two inactive sectors 13. Each transducer 9 is a cylindrical segment able to treat 44° of the circumference of the ciliary body, with an internal diameter of 12.8 mm and an external diameter of 27 mm.

The inactive sectors 13 correspond to two zones of the eye (called the naso-temporal axis zones) comprising nerve terminations and vascularisations. Thus the arrangement of transducers of the present invention allows avoiding the treatment of these zones.

It will be understood that the dimensions and arrangement of the transducers is a function of the diameter of the eye to be treated and of the size of the ciliary body (which differ from one type of animal to the other). The dimensions of each transducer are defined so as to obtain a lesion volume comprised between 3 mm$^3$ and 6 mm$^3$. The dimensions of the lesions obtained with each transducer can be calculated using simulation software developped by INSERM U556 on the basis of the Bio Heat Transfer Equation.

The transducers of a pair can be separated by 0.2 mm from each other along the internal diameter. The width of each transducer is less than 5 mm, and preferably equal to 4.5 mm. The length of each transducer 9 can be comprised between 7 mm and 9 mm, and preferably equal to 8.1 mm. The radial radius of curvature of each transducer 9 can be comprised between 9 mm and 11 mm, and preferably equal to 10.2 mm. The thickness of each transducer can be comprised between 0.1 mm and 0.4 mm and is preferably equal to 0.25 mm. For a piezoceramic transducer with a nominal frequency of 7 MHz, it will be used at its third harmonic. It will be noted that the standing crown 8 can comprise two or more transducers 9 distributed among the circumference in any manner without departing with the scope of the invention.

The transducers 9 are successively activated by the control unit 3 to destroy the ciliary body over the whole or a part of its circumference, each transducer 9 providing an internal injury in a shape compatible with the shape of the ciliary bodies of an arc of circle (i.e. lesions in the form of straight lines within an octagon).

In this embodiment, adapted to the treatment of glaucoma, the internal diameter of the proximal end of the sawn-off cone element 1 is sensibly equal to the corneal diameter plus 2 to 6 mm The internal diameter of the proximal end of the sawn-off cone element 1, depending on the patient corneal diameter, is comprised between 12 and 18 mm and the internal diameter of the distal end of the sawn-off cone element is comprised between 26 and 34 mm.

Moreover, the height of the sawn-off cone element 1 is comprised between 8 and 12 mm. In this manner, by positioning correctly the sawn-off cone element 1 onto the eye to be treated, as described hereinafter, the whole or a part of the ciliary body of the eye will be injured by HIFU energy without the need to manipulate the device during the treatment.

To apply correctly the sawn-off cone element 1 onto the eye, referring to FIG. 5, the surgeon must manipulate the sawn-off cone element 1 as far as the iris ring and the periphery of the cornea are centred in the distal opening of the sawn-off cone element 1 as illustrated in FIG. 5. If the white ring corresponding to the visible part of the sclera trough the opening of the proximal end of the ring, has a constant thickness, the centring is correct. When the sawn-off cone element 1 is centred on the pupil, the revolution axis of said sawn-off cone element 1 and the optical axis of the eye are merging, referring to FIG. 6. Consequently, the planes in which extend the distal edge and the proximal edge of the sawn-off cone element 1 are perfectly parallel to the planes of the eye such as iris plane, pupil plane or plane of the ciliary body, and the proximal edge of the sawn-off cone element 1 is at the plumb of the ciliary body. This allows a better positioning of the device according to the invention with regard to the lesions obtained (unlike the apparatus described in U.S. Pat. No. 4,484,569 and DE 44 30 720), and improves the reproducibility of the treatment.

Moreover, the device can comprise two aiming wires 14 extending crosswise and diametrally from the internal edge of the standing crown 8 or another centring system like a circular pad supposed to be centred on the pupil. This allows facilitating the centring of the sawn-off cone element with regard to the eye. To centre the sawn-off cone element 1, it is necessary to centre the intersection of the aiming wires 14 with the centre of the pupil.

It will be understood that the device according to the invention can comprise other centring system known from the man skilled in the art for facilitating the centring of the sawn of cone.

When the sawn-off cone element 1 is correctly centred onto the eye, the suction device 6 is activated to interlink said sawn-off cone element 1 with the eye. The depression into the annular groove 5 provides a deformation of the conjunctiva of the eye, said deformation forming an o-ring in the annular groove 5. This insures a proper maintain in position of the device during all the treatment.

The sawn-off cone element 1 is then filled with a physiological saline degassed solution, referring to FIG. 7, the o-ring formed by the deformation of the conjunctiva of the eye in the annular groove ensuring the sealing. The physiological saline solution provides a cooling of the eye and the device during the generation of HIFU and an ultrasound coupling media that permits the propagation of ultrasound from transducers 9 to area of interest, i.e. the ciliary body. Note that the physiological saline solution moisturizes the cornea of the eye during the treatment.

It is obvious that the physiological saline degassed solution could be substituted by any ultrasound coupling agent such as aqueous media or lipophilic media without departing of the scope of the invention.

Then, the frequency and/or the power and/or the duration of each pulse are selected or already predetermined and the transducers 9 are successively activated by the control unit to destroy the ciliary body over the whole or a part of the circumference. Preferably, each transducer is elongated so that each transducer provides an internal injury in the shape of straight lines or arc of circle as represented in FIG. 8. Note that, in FIG. 8, the X-Y plane represents the free end of the eyeglobe and that the height represents the depth of the eye globe. The use of elongated transducers allows producing unpunctual lesions more extended than the punctual lesions obtained with the apparatuses described in U.S. Pat. No. 4,484,569 and DE 44 30 720. This improves the efficiency of the treatment since it remains less non-destroyed tissues (with regard to results obtained with the apparatuses described in U.S. Pat. No. 4,484,569 and DE 44 30 720).

Note that the treatment according to the invention is advantageously an ambulatory treatment whose duration is about 2 minutes for the patient.

According to another embodiment of the invention, referring to FIG. 9, the device comprises in the same manner as preceding a sawn-off cone element 1 opened at both ends wherein the small base is the proximal end and the large base is the distal end and means 2 to generate high intensity focused ultrasound beam, said means being fixed on the distal end of the sawn-off cone element 1. Said means 2 consist in a standing crown 8 holding a plurality of transducers 9 wherein the external radius of said standing crown 8 is sensibly equal to the internal diameter of the distal end of the sawn-off cone element 1. The external edge of the standing crown 8 of transducers 9 comprises an annular groove 10 cooperating with an annular lug 11 extending in the sawn-off cone element 1 at the vicinity of it's distal end in such a way that the standing crown 8 is retained at the distal end of the sawn-off cone element 1. In this way, the standing crown 8 extends toward the revolution axis of said sawn-off cone element 1.

Said transducers 9 are held in the proximal edge of the standing crown 8. Moreover, each transducer 9 is a flat segment having a globally rectangular profile that extends sensibly parallel to the proximal and distal edge of the sawn-off cone element 1.

Moreover, the device comprises a focusing acoustic lens 15 extending under said transducers 9, i.e. held by the standing crown 8 and extending between the proximal edge of the standing crown 8 and the proximal edge of the sawn-off cone element 1. Said focusing acoustic lens presents a cylindrical shape and a concave edge wherein the concavity is tuned towards the eyeglobe, and more particularly towards the ciliary body as shown in FIG. 9, to focalize HIFU onto the area of interest, i.e. the ciliary body of the eye.

The standing crown 8 comprises an annular channel 16 in which extends the connecting cables of the transducers 9, not shown in FIG. 9.

As disclosed previously, referring to FIG. 4, the standing crown 8 of transducers 9 comprises two pairs of three transducers 9 separated by two inactive sectors 13. Each transducer 9 is an annular segment of 44° with an internal diameter of 12.8 mm and an external diameter of 24.3 mm.

It is obvious that means to generate high intensity focused ultrasound energy can consist in at least two transducers having a cylindrical segment shape, fixed on the distal end of the sawn-off cone element in such a way that said transducers extend toward the revolution axis of said sawn-off cone element.

Moreover, said means to generate high intensity focused ultrasound energy can be substituted by means to generate high intensity dynamically focused ultrasound energy consisting in at least two annular array transducers having a toric segment shape, fixed on the distal end of the sawn-off cone element in such a way that said annular array transducers extend toward the revolution axis of said sawn-off cone element.

The device according to the invention can be used for treatment of open angle glaucoma, but with a different approach than cyclodestruction. Indeed as described in WO 2008/024795, ultrasound can be used for their vibrating properties on small particles. In patients with too high intra ocular pressure, and with open angle glaucoma, the problem is that the trabecular meshwork is no longer efficient enough to allow aqueous humor to be drained properly to Schlemm's canal. Trabeculum permeability is lower than normally, due to the fact that trabecular spaces are blocked with small particles as pigments, cell debris, fibrin, etc. . . . .

The device according to the invention can easily produce a vibration obtained with the propagation of an ultrasonic beam, transmitted to the trabecular meshwork, which unlike the apparatus described in WO 2008/024795 can concern the whole circumference of the trabeculum at the same time, more rapidly and in only one step. Moreover, with the device according to the invention, thanks to the ring which allows centering and fixation on the eye globe, this technique can be substantially improved compared to the device described in WO 2008/024795.

In the case where the device according to the invention is used to produce vibration, the power is lower and the duration of the energy generated by each transducer is shorter than previously explained, and is repeated periodically with many burst successively. For instance, the duration of the energy generated by each annular transducer is less than 10 seconds, and more preferably less than 5 seconds, the application of is repeated 2 times or more.

Indeed, in such case, the aim is no longer to produce lesions (i.e. destroy the target region as explained with reference to the ciliary bodies) but to produce vibration. So it is necessary to limit the duration of the energy generated in order to ensure that the target region (i.e. the trabeculum in the present case) is not burned.

Another embodiment of the device according to the invention, used as a treatment of open angle glaucoma with the vibration technique applied on the trabecular meshwork, can be combined with a phacoemulsification machine. In fact when the particles like cell debris, fibrin, pigment or other, responsible for the loss of drainage efficiency of trabeculum, are delivered from their adherence to the trabecular meshwork, and are circulating in the aqueous humor it is obvious that they will rapidly be cached again by trabeculum, reducing consequently the efficiency of the treatment by the vibration technique. The idea for this preferred embodiment, is to combine this treatment with a phacoemulsification machine, and preferably during a cataract surgery, because during this surgery the anterior chamber and the liquid it contains, are completely washed with a balanced salt solution circulating in the irrigation/aspiration circuit, so that if the vibration technique is performed before the cataract surgery, all the debris delivered from their adherence on the trabecular meshwork, will be washed out of the anterior chamber, increasing the efficiency of the treatment. It is well known that cataract surgery is more frequent in older population. It is well known too that glaucoma is more frequent in the same population. For this reason, combined surgeries, including cataract and trabeculectomy are more and more frequent. The idea for this preferred embodiment, is to add a new feature to the phacoemulsification machines, already often equipped with vitrectomy features, which will be the glaucoma prevention by a systematic cleaning of the trabeculum with the ultrasound vibration technique, when a cataract surgery is performed in a patient with a too high intra ocular pressure (>15-18 mm Hg).

It is obvious that the device according to the invention could be adapted for other ocular pathology such as for a cataract surgery by focusing the HIFU onto the crystalline lens rather than onto the ciliary body.

The goal of the cataract surgery is to replace the natural crystalline lens by an artificial lens, when the natural crystalline lens has lost its transparency. In a first step, it is necessary to remove the natural lens surgically. According to the prior art, this extraction is performed by a phacoemulsification procedure. The surgeon uses a machine equipped with an ultrasonic hand piece. The tip of the hand piece sculpts the crystalline lens and simultaneously irrigates and sucks the lens debris.

By adapting the device according to the invention by focusing the HIFU onto the crystalline lens rather than onto the ciliary body, the cataract surgery by a phacoemulsification procedure could be made easier, faster and more accurate. The device could be used advantageously before the surgery to modify the consistence of the crystalline lens and to reduce the adherence between the cortex and the capsular bag. This could be done in order to: reduce the dimension of the corneal incision, reduce the duration of the surgery and increase the quality of the extraction by reducing the quantity of residual cortex, which is responsible for postoperative capsular bag opacification.

According to a last embodiment of the invention particularly adapted to facilitate penetration of pharmaceutical agents in the eye, referring to FIG. 10, the device comprises in the same manner as preceding a sawn-off cone element 1 opened at both ends wherein the small base is the proximal end and the large base is the distal end and means 9 to generate scattered ultrasound beam, said means being fixed on the distal end of the sawn-off cone element 1.

Such technique as described in WO 2007/081750, could be particularly useful to avoid intra vitreal injection of pharmaceutical agents, for treating chronic or acute eye diseases. But the cited invention doesn't describe a device adapted to the eye globe intended to facilitate the manipulation, and with a large area surface covered by high intensity ultrasound. The present embodiment of the invention as described above, could facilitate the manipulation with the use of a centring and fixation ring, and increase the efficacy of the treatment thanks to a larger area covered by the ultrasound beam.

Said means 17 consist in a standing crown 8 holding a plurality of transducers 9 wherein the external radius of said standing crown 8 is sensibly equal to the internal diameter of the distal end of the sawn-off cone element 1. The external edge of the standing crown 8 of transducers 9 comprises an annular groove 10 cooperating with an annular lug 11 extending in the sawn-off cone element 1 at the vicinity of it's distal end in such a way that the standing crown 8 is retained at the distal end of the sawn-off cone element 1. In this way, the standing crown 8 extends toward the revolution axis of said sawn-off cone element 1.

Said transducers 9 are held in the proximal edge of the standing crown 8. Moreover, each transducer 9 is an annular segment suitable to generate scattered ultrasound beam into the sawn-off cone element 1, said sawn-off cone element 1 being filed with a coupling media 18 such as physiological saline degassed solution containing a pharmaceutical formulation and/or micro carriers.

In this non limited example, said transducers 9 has a globally rectangular profile that are inclined globally toward the centre of the proximal edge of the sawn-off cone element 1.

It is obvious that means to generate scattered ultrasound beam can be means to generate high intensity non focused ultrasound energy consisting in at least two transducers having an annular or rectangular flat segment shape, fixed on the distal end of the sawn-off cone element in such a way that said transducers extend toward the revolution axis of said sawn-off cone element 1.

Said transducers 9 are circumferentially placed over the whole or a part of the circumference of the standing crown 8.

When the sawn-off cone element 1 is applied onto the eye, the iris ring and the cornea perimeter are globally centred in the distal opening of the sawn-off cone element 1. Then, the suction device 6 is activated to interlink said sawn-off cone element 1 with the eye. The depression into the annular groove 5 provides a deformation of the conjunctiva of the eye, said deformation forming an o-ring in the annular groove 5.

The sawn-off cone element 1 is then filled with a physiological saline degassed solution containing the appropriate pharmaceutical agents, the o-ring formed by the deformation of the conjunctiva of the eye in the annular groove ensuring the sealing.

Then, the frequency and/or the power and/or the duration of pulses are selected or already predetermined and the transducers 9 are successively or simultaneously activated by the control unit to increase the porosity of the cornea and of the sclera of the eye and to homogenise the pharmaceutical agent in the coupling media, by mixing it, that enhance the transport rate of the pharmaceutical agents across the cornea an scleral tissues reaching the anterior and posterior segments of the eye and avoiding intra ocular injections.

Note that the device according to the invention could be used in case of any medical treatment of eye diseases with local drug administration. Usually this kind of treatment is administered topically with eye drops. The problem is that eye drops must be administered many times per day, which is a constraint and often leads to the patient's demotivation, even if new drugs formulations have recently reduced in some cases to once a day the number of eyedrops administrations. Other kinds of treatments require intra-vitreal injections of the drugs directly in the eye.

Using high intensity ultrasound to facilitate drug penetration in biologic tissues according to the invention leads to increased action duration, a reduction of the doses administered and a better efficacy.

The device according to the invention could be used for example to avoid intra-vitreal injections of antibiotics, anti viral drugs, anti inflammatory drugs, chemotherapy agents or new molecules like anti-angiogenics for the treatment of diabetic macular edema or of age related macular degeneration. The intra-vitreal injections are of potential high risk. The geometric shape of our device could allow its filling with a liquid containing active drug. A particular model of the device designed to produce a non focused ultrasound beam, with a low power which doesn't generate lesions in the tissues could allow the penetration of active drugs in the intraocular structures.

Moreover, note that the standing crown 8 holding means 9 to generate scattered ultrasound beam is advantageously removable and can be substituted by a standing crown 8 holding means 2 to generate HIFU beam as disclosed in FIGS. 2 and 9.

This written description uses examples to disclose the invention, including the best mode, and also to enable any person skilled in the art to make and use the invention. The scope of the subject matter described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A device to treat an ocular pathology, comprising
at least one eye ring wherein a proximal end of said eye ring is configured to be applied onto an eye globe and
an ultrasound beam generator for generating high intensity focused ultrasound, said ultrasound beam generator being fixed on a distal end of the eye ring, and wherein the ultrasound beam generator comprises at least two transducers extending toward a revolution axis of said at least one eye ring, wherein each transducer has a rectangular profile and presents a cylindrical segment shape configured to be tuned towards the eye globe, the transducers being distributed circumferentially,
wherein the device is configured to treat the whole circumference of the eye in only one step by applying high intensity focused ultrasound onto the eye,
wherein the ultrasound beam generator comprises a standing crown holding the at least two transducers, said standing crown being fixed on the distal end of the eye ring in such a way that the transducers extend toward the revolution axis a said eye ring, and
wherein an external annular flange comprises a concave profile having a radius of curvature configured to be fit to curvature of the eye globe.

2. The device according to claim 1, wherein the width of each transducer is 4.5 millimeters.

3. The device according to claim 1, wherein the ultrasound beam generator comprises a plurality of transducers arranged according to a treatment pattern.

4. The device according to claim 3, wherein said transducers are placed peripherally over the standing crown according to the treatment pattern.

5. The device according to claim 3, wherein said transducers are placed peripherally over the whole or a part of the standing crown.

6. The device according to claim 3, wherein said transducers are circumferentially placed over the whole or a part of the circumference of the standing crown.

7. The device according to claim 1, wherein the standing crown comprises an annular groove disposed at an external edge of the standing crown to be coupled with an annular lug disposed at the distal end of the eye ring.

8. The device according to claim 7, wherein an external radius of the standing crown is equal to the internal diameter of the distal end of the eye ring.

9. A method for treating an ocular pathology comprising applying high intensity focused ultrasound onto the eye using the device according to claim 1.

10. A device to treat an ocular pathology comprising
at least one eye ring wherein a proximal end of said eye ring is configured to be applied onto an eye globe and
an ultrasound beam generator for generating high intensity focused ultrasound, said ultrasound beam generator being fixed on a distal end of the eye ring, and wherein the ultrasound beam generator comprises at least two transducers wherein each transducer is a flat segment having a rectangular profile that extends parallel to the proximal and distal edges of the eye ring, and at least two focusing acoustic elements extending under a respective transducer, where each focusing acoustic element presents a cylindrical segment shape configured to be tuned towards the eye globe, the transducers being distributed circumferentially,
wherein the device is configured to treat the whole circumference of the eye in only one step,
wherein the ultrasound beam generator comprises a standing crown holding the at least two transducers, said standing crown being fixed on the distal end of the eye ring in such a way that the transducers extend toward the revolution axis of said eye ring, and
wherein an external annular flange comprises a concave profile having a radius of curvature configured to be fit to curvature of the eye globe.

11. The device according to claim 10 wherein the standing crown holds the at least two transducers and the at least two focusing acoustic elements, said standing crown being fixed on the distal end of the eye ring in such a way that the at least two focusing acoustic elements extend toward the revolution axis of said eye ring.

12. The device according to claim 10 wherein the width of each focusing acoustic element is 4.5 millimeters.

13. A device to treat an ocular pathology, comprising
at least one eye ring wherein a proximal end of said eye ring is configured to be applied onto an eye globe and
an ultrasound beam generator for generating high intensity focused ultrasound, said ultrasound beam generator being fixed on a distal end of the eye ring, and wherein the ultrasound beam generator comprises at least two transducers extending toward a revolution axis of said at least one eye ring, wherein each transducer has a rectangular profile and presents a cylindrical segment shape configured to be tuned towards the eye globe, the transducers being distributed circumferentially, wherein the device is configured to treat the whole circumference of the eye in only one step by applying high intensity focused ultrasound onto the eye, wherein the ultrasound beam generator comprises a standing crown holding the at least two transducers, said standing crown being fixed on the distal end of the eye ring in such a way that the transducers extend toward the revolution axis of said eye ring, and wherein the standing crown comprises an annular groove disposed at an external edge of the standing crown to be coupled with an annular lug disposed at the distal end of the eye ring.

* * * * *